(12) United States Patent
Kelly et al.

(10) Patent No.: US 6,432,974 B1
(45) Date of Patent: Aug. 13, 2002

(54) PYRROLO-ISOQUINOLINE AND TETRA-HYDROPYRROLO-ISOQUINOLINE DERIVATIVES AND THEIR USE AS MEDIATORS OF THE 5-HT7 RECEPTOR

(75) Inventors: Michael G. Kelly, Thousand Oaks, CA (US); Young H. Kang, Robbinsville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/771,316

(22) Filed: Jan. 26, 2001

Related U.S. Application Data

(60) Provisional application No. 60/266,311, filed on Feb. 4, 2000.

(51) Int. Cl.⁷ .................. A61K 31/4745; C07D 471/04; A61P 25/00
(52) U.S. Cl. .......................................... 514/292; 546/84
(58) Field of Search ............................. 546/84; 574/292

(56) References Cited

U.S. PATENT DOCUMENTS 4,260,762 A * 4/1981 Berger .......................... 546/84
4,442,291 A   4/1984 Berger et al.

OTHER PUBLICATIONS

Vanhoenacker P et al. Trends in Pharmacological Sciences. (Feb. 2000). 21(2), pp. 70–77.*
C.A. 131: 318141 XP002164267 (1999).
C.A. 127: 273150 XP002164268 (1997).
C.A. 127: 171786 XP002164269 (1997).
C.A. 123: 189133 XP992164270 (1995).
C.A. 121: 222193 XP002164271 (1994).
C.A. 120: 1074 XP002164272 (1993).
C.A. 130: 276228 XP002164273 (1999).

* cited by examiner

*Primary Examiner*—Evelyn Mei Huang
(74) *Attorney, Agent, or Firm*—Rebecca R. Barrett

(57) ABSTRACT

Compounds of the formula

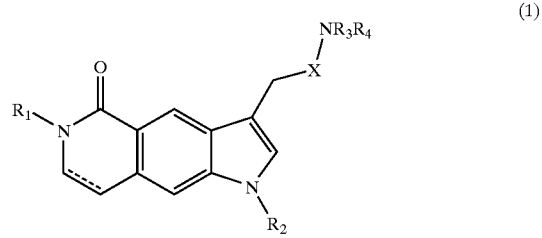

are useful in the treatment of anxiety, depression and related disorders of the central nervous system and other conditions such as schizophrenia, sleep disorders, including instances of circadian rhythm, the treatment of alcohol and drug withdrawal and sexual dysfunction.

7 Claims, No Drawings

PYRROLO-ISOQUINOLINE AND TETRA-HYDROPYRROLO-ISOQUINOLINE DERIVATIVES AND THEIR USE AS MEDIATORS OF THE 5-HT7 RECEPTOR

This application claims the benefit of U.S. Provisional Application No. 60/266,311, filed Feb. 4, 2000.

BACKGROUND OF THE INVENTION

The recently identified human 5-hydroxytryptamine-7 (5-HT7) receptor subtype has been cloned, and the extensive distribution of its mRNA has been reported. Highest levels of 5-HT7 receptor mRNA have been observed in the hypothalamus, thalamus, brainstem and hippocampus, while lower levels have been found in the cerebral cortex, striatum, olfactory bulb and olfactory tubercle. The presence of 5-HT7 mRNA is not limited to the brain, it has also been found in peripheral tissues, namely spleen, stomach, ileum, intestine, coronary artery, descending colon, smooth muscle cells and heart.

Distribution and pharmacological studies have suggested that the 5-HT7 receptor may be involved in the vasodilation of blood vessels, and therefore may play a role in cardiovascular indications. 5-HT7 receptors also play a role in the control of circadian rhythms of spontaneous electrical activity in the suprachiasmatic nucleus. The high affinity of a number of antipsychotic agents for the 5-HT7 receptor suggests that this receptor may help mediate the therapeutic actions of these compounds.

Octahydro-pyrrolo-isoquinoline derivatives, as antipsychotic neuroleptic agents are disclosed in EP 10661 having the formula:

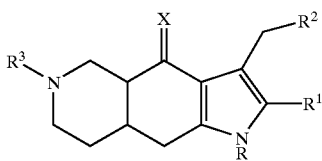

where R2 is hydrogen, alkyl, cycloalkyl, alkenyl, acyl, aryl or aralkyl.

Ancilated indole derivatives as antiphlogistics are disclosed in DE 77-2740836 having the formula:

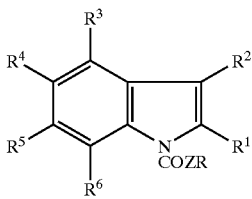

wherein:
R is phenyl or heterocycle,
$R^1$, $R^2$ are alkyl, carboxyalkyl, phenyl, and
$R^3$, $R^4$ is a 5 or 6 membered ring optionally containing 1–3, 5, O or N atoms.

A series of novel 3-(2-aminoethyl)-pyrrolo[2,3-g] isoquinolin-5-one derivatives are claimed that are effective pharmaceuticals for the treatment of anxiety, depression and related CNS disorders and other conditions such as schizophrenia, sleep disorders, including instances of circadian rhythm, the treatment of alcohol and drug withdrawal and sexual dysfunction.

SUMMARY OF THE INVENTION

This invention relates to novel 3-(2-aminoethyl)-pyrrolo [2,3-g]isoquinolin-5-one derivatives, to processes for their preparation, to pharmaceutical compositions containing them and to their use in therapy. The compounds are believed to be useful for the treatment of CNS disorders such as anxiety, depression and related CNS conditions and other conditions such as schizophrenia, sleep disorders, including instances of circadian rhythm, migraine headaches, the treatment of alcohol and drug withdrawal and sexual dysfunction by virtue of their ability to bind to the 5-HT7 receptor subtype. The compounds of the present invention may also find utility in the treatment of cardiovascular and septic shock, hypotension, renal disorders, diarrhea and spastic colon.

Compounds of the present invention are represented by the general formula

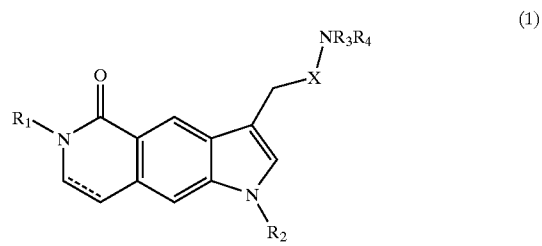

wherein:
R1 is hydrogen, alkyl of 1 to 8 carbon atoms, cycloalkyl of 3 to 8 carbon atoms, heterocycloalkyl of 3 to 8 members, alkylcycloalkyl of 4 to 9 carbon atoms, alkylheterocycloalkyl of 4 to 9 members or (CH2)mAr or (CH2)mHet;

R2 is hydrogen, alkyl of 1 to 8 carbon atoms, (CH2)nAr or (CH2)nHet;

R3 is hydrogen, alkyl of 1 to 8 carbon atoms, alkylcycloalkyl of 4 to 9 carbon atoms, alkylheterocycloalkyl of 4 to 9 members, (CH2)nAr or (CH2)nHet;

R4 is hydrogen or alkyl of 1 to 8 carbon atoms;

R is hydrogen or alkyl of 1 to 4 carbon atoms;

X is [(CH=CH)R]n, (CH$_2$)n, or [(C≡C)R]n, CHR(CH$_2$) n, CR$_2$(CH$_2$)n;

a dashed line represents an optional double bond;

m is an integer selected from 1 or 2; and n is an integer selected from 0, 1 or 2, or a pharmaceutically acceptable salt thereof.

In some preferred aspects of the present invention R1 is hydrogen, alkyl of 1 to 8 carbon atoms, alkylcycloalkyl of 4 to 9 carbon atoms, alkylheterocycloalkyl of 4 to 9 members, (CH2)nAr or (CH2)nHet.

In other embodiments of the present invention R2 is hydrogen or alkyl of 1 to 8 carbon atoms.

X is preferably (CH2)n, and the optional double bond is preferably absent.

R3 and R4 are preferably hydrogen or alkyl.

Alkyl refers to straight or branched chain alkyl.

Cycloalkyl refers to a saturated ring of 3 to 8 carbon atoms and preferably 5 to 6 carbon atoms such as cyclopentyl and cyclohexyl.

Heterocycloalkyl refers to a saturated ring of 3 to 8 carbon atoms having 1 or 2 heteroatoms selected from N, O and S. Preferably, heterocycloalkyl refers to 5 or 6 membered rings having at least one nitrogen heteroatom such as piperidinyl, piperazinyl, pyrrolidinyl, imidazolidinyl, morpholinyl, thiomorpholinyl, and pyrazolidinyl.

Ar is aryl and preferably is phenyl or naphthyl which may optionally be substituted by one or more groups selected from flourine, chlorine, bromine, iodine, hydroxy, alkyl of 1 to 6 carbon atoms, trifluoromethyl, cyano and amino.

Het refers to heteroaryl and refers to a monocyclic 5 or 6 membered heteroaryl group or a 9 or 10 membered bicyclic heteroaryl group. Preferred heteroaryls have 1 or 2 heteroatoms selected from N, O and S, and, when 2 heteroatoms are present, it is preferred that at least one heteroatom is nitrogen. Exemplary monocyclic heteroaryl groups include pyridinyl, pyriminidinyl, pyrazinyl, furyl, thienyl, pyrrolyl, indolyl. Exemplary bicyclic heteraryl groups include benzodioxanyl or quinolyl. Heteroaryl groups may optionally be substituted with one or more groups selected from flourine, chlorine, bromine, iodine, hydroxy, alkyl of 1 to 6 carbon atoms, trifluoromethyl, cyano and amino.

The pharmaceutically acceptable salts are the acid addition salts which can be formed from a compound of the above general formula and a pharmaceutically acceptable acid such as phosphoric, sulfuric, hydrochloric, hydrobromic, citric, maleic, fumaric, acetic, lactic or methanesulfonic acid.

The compounds of this invention contain a chiral center, providing for various steroisomeric forms such as racemic mixtures as well as optical isomers. The individual optical isomers can be prepared directly or by asymmetric or sterospecific synthesis or by conventional separation of optical isomers from the racemic mixture.

DETAILED DESCRIPTION OF THE INVENTION

Compounds of the present invention may be prepared by those skilled in the art of organic synthesis employing conventional methods which utilize readily available reagents and starting materials. For example, reaction of an acidic solution (e.g. methanesulfonic acid) of 5-fluoroindanone with sodium azide affords the required Schmidt rearrangement product. This can be alkylated with alkyl halides, alkylaryl halides or alkylheteroaryl halides under the influence of a base such as sodium hydride, and the product can be treated with hydrazine hydrate to afford the required aryl hydrazine. Reaction of the 1-aryl substituted hydrazine with a substituted aldehyde derivative or protected derivative thereof (e.g. enol ether or dioxolan protecting group) under Fisher indole synthesis condition affords the 3-substituted-pyrrolo[2,3-g]isoquinolin-5-one compound. 2-(3-chloropropyl)-1,3-dioxolan is an example of suitably substituted and protected aldehyde derivative, and dilute sulfuric acid or dilute hydrochloric acid are suitable catalysts or co-solvents for the reaction. The basic amine may be alkylated directly for example by the reaction of an alkyl halide or alkylaryl halide under the influence of a base such as sodium hydride, or alternatively the basic amine may be directly acylated by the action of carboxylic acid halides, and the subsequent amide can be reduced by the action of lithium aluminum hydride. These step may be repeated to provide bis-alkylated derivatives. The pyrrol nitrogen may be alkylated with alkyl halides or alkylaryl halides or alkylheteroaryl halides under the influence of a base such as sodium hydride. The optional double bond can be introduced by known and conventional methods. For example reaction of a 3-substituted-1,6,7,8-tetrahydropyrrolo[2,3-g]isoquinolin-5-one with 2,3-dichloro-5,6-dicyanobenzoquinone (DDQ) affords the required 3-substituted-pyrrolo[2,3-g]isoquinolin-5-one compound of the present invention.

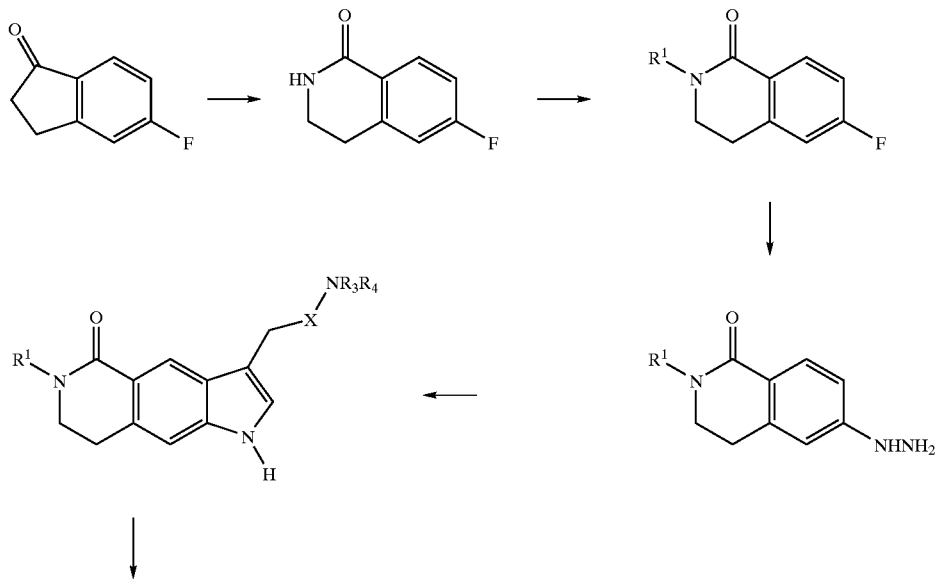

-continued

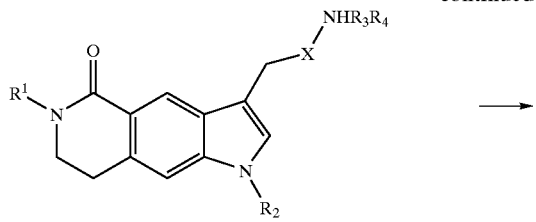 → 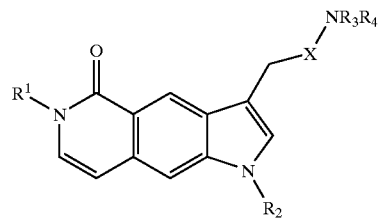

Compounds of the present invention bind with very high affinity to the 5-HT7 receptor and consequently, they are useful for mediating the 5-HT7 receptor in mammals. Compounds of the present invention are useful in the treatment of central nervous system disorders associated with dysfunction of the 5-HT7 receptor such as anxiety, depression and related conditions (e.g. GAD) and other conditions such as schizophrenia, sleep disorders, including instances of circadian rhythm, migraine headaches, the treatment of alcohol and drug withdrawal and sexual dysfunction by virtue of their ability to bind to the 5-HT7 receptor subtype. Similarly, the compounds of the present invention may also find utility in the treatment of cardiovascular and septic shock, hypotension, renal disorders, diarrhea and spastic colon.

5-HT7 Receptor Binding Assay

High affinity for the serotonin 5HT7 receptor was established by testing the claimed compound's ability to displace [$^3$H] LSD binding in CHO cells stably transfected with the human 5HT7 receptor. Human cloned receptor membranes of the serotonin-7 subtype, expressed in a Chinese Hamster Ovary (CHO) cell line are purchased from BioSignal Drug Discovery Technology, Montreal, Canada. The frozen ampoules of receptor membranes are reconstituted in 50.0 mM Tris.HCl buffer, at pH 7.4 to give 15–20 $\mu$g of tissue protein per 100.0 $\mu$l of suspension. The diluted membranes are kept cold on ice and immediately used in subsequent binding experiments.

Binding experiments are performed in a 96 well microtiter plate format, in a total volume of 200 $\mu$l. To each well is added: 80.0 $\mu$l of incubation buffer made in 50 mM Tris.HCl buffer, pH 7.4 and containing 10.0 mM MgCl2 and 0.5 mM EDTA; 20 $\mu$l of [$^3$H] LSD (S.A., 86.0 Ci/mmol, Amersham Life Science), 5.0–6.0 nM. The dissociation constant, $K_D$ of [$^3$H]LSD at the human serotonin 5-HT7 receptor is 2.9 nM, as determined in saturation studies with increasing concentrations of [$^3$H]LSD. The reaction is initiated by the final addition of 100.0 $\mu$l of tissue suspension. Non-specific binding is measured in the presence of 10.0 $\mu$M methiothepin, added in 20.0 $\mu$l volume.

Test compounds when needed are added in 20.0 $\mu$l volume. The reaction proceeds in the dark for 120 minutes at room temperature, at which time, the bound ligand receptor complex is filtered off on a 96 well unifilter with a Packard[R] Filtermate 196 Harvester. The filtermate is air dried and the radioactivity is measured in a Packard TopCount[R] equipped with six photomultiplier detectors, after drying and addition of 40.0 $\mu$l Microscint[R]-20 scintillant to each shallow well. The unifilter plate is heat sealed and counted in a Packard TopCount[R] with a tritium efficiency of 31.0%. Specific binding is defined as the total radioactivity bound less the amount bound in the presence of 10.0 $\mu$M unlabeled methiothepin. Binding in the presence of varying concentrations of test drugs is expressed as percent of specific binding in the absence of drug. These results are then plotted as log % bound vs log concentration of test drug. Nonlinear regression analysis of data points with a computer assisted program Prism[R] yields both the IC$_{50}$ and the K$_i$ values of test compounds with 95% confidence limits. Alternatively, linear regression line of decline of data points is plotted, from which the IC$_{50}$ value can be read off and the K$_i$ value determined by solving the following equation:

$$K_i=IC_{50}/(1+L/K_D)$$

where L is the concentration of the radioactive ligand used and $K_D$ is the dissociation constant of the ligand for the receptor, both expressed in nM.

Reference Compounds tested using the above procedure: K$_i$ value and 95% confidence interval

| Compound | 5-HT7 binding Ki (nM) |
|---|---|
| Clozapine | 6.3 (2.6–11.0) nM |
| Loxapine | 43.0 (26.0–68.0) nM |

The compounds of the present invention showed activity in the above test, for example:

| Compound | 5-HT7 binding Ki (nM) |
|---|---|
| Compound 1 | 14 |

The following non-limiting specific examples are included to illustrate the synthetic procedures used for preparing compounds of formula 1. In these examples, all chemicals and intermediates are either commercially available or can be prepared by standard procedures found in the literature or are known to those skilled in the art of organic synthesis. Several preferred embodiments are described to illustrate the invention. However, it should be understood that the invention is not intended to be limited to the specific embodiments.

Intermediate 1

6-Fluoro-3,4-dihydro-2H-isoquinolin-1-one

Sodium azide (7.8 g, 120 mmol) was added portionwise to a stirred solution of 5-fluoro indanone (9 g, 60 mmol) in methanesulfonic acid (35 mL) and dichloromethane (35 mL), while the temperature was maintained between 22°–29° C. Once addition was completed, the mixture was stirred at room temperature for 16 hours. The mixture was cooled to 0° C. and neutralized by the addition of 5N-NaOH solution and the organic layer separated. The aqueous layer was washed with dichloromethane (3×50 mL) and the combined organics washed with water (50 mL), brine (50 mL) and dried over anhydrous sodium sulfate. Filtration and concentration gave a light oil (7.8 g) which was purified by flash silica gel chromatography (eluted with diethyl ether) to afford the titled compound as a white solid.

m.p. 107–108° C.

M+ 165

Elemental Analysis for: $C_9H_8FNO$ Calculated: C, 65.45; H, 4.88; N, 8.48, Found: C, 65.01; H, 5.10; N, 8.33.

Intermediate 2

6-Hydrazino-3,4-dihydro-2H-isoquinolin-1-one

A solution of 6-fluoro-3,4-dihydro-2H-isoquinolin-1-one (3.6 g, 0.022 mole) and hydrazine (17.3 mL, 0.55 mole) was stirred at reflux in dioxane (150 mL) under nitrogen for 48 hours. The reaction mixture was concentrated under vacuo, water added (150 mL), and the product isolated by filtration. The product was thoroughly washed with diethyl ether to give the titled compound quantitatively as a white solid.

m.p. 158–160° C.

MS(EI) m/e 177 (M+)

Elemental Analysis for: C9H11N3O 0.75H$_2$O Calculated: C, 56.68; H, 6.61; N, 22.03. Found: C, 56.69; H, 6.11; N, 22.23.

Compound 1

3-(2-Amino-ethyl)-1,6,7,8-tetrahydro-pyrrolo[2,3-g]isoquinolin-5-one

A solution of 6-hydrazino-3,4-dihydro-2H-isoquinolin-1-one (0.5 g, 2.3 mmole) and 2-(3-chloropropyl)-1,3-dioxolan (0.31 mL, 2.3 mmole) was stirred at reflux in degassed EtOH/H$_2$O (5/1, 90 mL) solution under nitrogen for 24 hours. The reaction mixture was partitioned between saturated aqueous NaHCO$_3$ and isopropyl acetate. The combined organic layers were dried over anhydrous sodium sulfate and concentrated for chromatography on a silica gel column using CH$_2$Cl$_2$/MeOH/NH$_4$OH (9.0/1.0/0.1) solution to give an oil. The oil containing two isomers was separated by Primesphere C-5 reversible preparative HPLC (90%CH$_3$CN/H$_2$O+0.1%TFA) and the desired product was freeze-dried under vacuo to give the titled compound as a yellow colored solid.

m.p. 82–86° C.

MS(ESI) m/e 230 (M+H)+

Elemental Analysis for: C13H15N3O.C2HF3O2. H2O Calculated: C, 49.86; H, 4.60; N, 11.24. Found: C, 49.98; H, 4.65; N, 11.39.

Compound 2

3-(2-Amino-ethyl)-6-benzyl-1,6,7,8-tetrahydro-pyrrolo[2,3-g]isoquinolin-5-one

A solution of 6-fluoro-3,4-dihydro-2H-isoquinolin-1-one (1.5 g, 9.1 mmole) and cesium carbonate (3.3 g, 10 mmole) in acetonitrile (100 mL) was stirred at room temperature under nitrogen. To this was added benzyl bromide (1.2 mL, 10 mmole) and the mixture refluxed for 15 hours. The reaction mixture was concentrated for chromatography on a silica gel column using EtOAc/hexane (9/1) to give the expected product, 2-N-benzyl-6-fluoro-3,4-dihydro-2H-isoquinolin-1-one, as an oil (2.2 g, 95%).

A solution of 2-N-benzyl-6-fluoro-3,4-dihydro-2H-isoquinolin-1-one (2.2 g, 8.6 mmole) and hydrazine (6.7 mL, 0.215 mole) was stirred at reflux in dioxane (150 mL) under nitrogen for 48 hours. The reaction mixture was concentrated for chromatography on a silica gel column by using EtOAc/MeOH (9/1) to give the expected product, 2-N-benzyl-6-hydrazino-3,4-dihydro-2H-isoquinolin-1-one, quantitatively as an oil.

A solution of 2-N-benzyl-6-hydrazino-3,4-dihydro-2H-isoquinolin-1-one (1.1 g, 4.1 mmole), 2-(3-chloropropyl)-1,3-dioxolan (0.6 mL, 4.1 mmole) and 1.0 M ethereal HCl (4.1 mL) was stirred at reflux in degassed EtOH/H$_2$O (5/1, 200 mL) solution under nitrogen for 24 hours. The reaction mixture was partitioned between saturated aqueous NaHCO$_3$ and isopropyl acetate. The combined organic layers were dried over anhydrous sodium sulfate and concentrated for a multiple chromatography on a silica gel column using CH$_2$Cl$_2$/MeOH/NH$_4$OH (9.0/1.0/0.1) solution to give a free base of the desired product as an off-white colored solid (0.35 g, 1.1 mmole, 27%). The product in methanol was treated with 1.0 M ethereal HCl (1.1 mL, 1.1 mmole) and recrystallized from CH$_2$Cl$_2$/MeOH (1/1) to afford the titled compound as an off-white colored solid.

m.p. 262–263° C.

MS(ESI) m/e 320 (M+H)+

Elemental Analysis for: C20H21N3O.HCl.H2O Calculated: C, 64.25; H, 6.47; N, 11.24. Found: C, 64.31; H, 6.09; N, 11.09.

Compound 3

3-(2-Amino-ethyl)-6-benzylpyrrolo[2,3-g]isoquinolin-5-one

A solution of 3-(2-Amino-ethyl)-6-benzyl-1,6,7,8-tetrahydro-pyrrolo[2,3-g]isoquinolin-5-one (1 mmole) and 2,3-dichloro-5,6-dicyanobenzoquinone (2 mmole) in chlorobenzene (15 mL) at reflux under nitrogen for 24 hours provides the titled compound as a yellow colored solid.

MS(ESI) m/e 228 (M+H)+

Elemental Analysis for: C13H13N3O Calculated: C, 68.70; H, 5.70; N, 18.49. Found: C, 68.51; H, 5.59; N, 18.29.

Compound 4

3-(2-N-Benzylamino-ethyl)-1,6,7,8-tetrahydro-pyrrolo[2,3-g]isoquinolin-5-one

A solution of 3-(2-amino-ethyl)-1,6,7,8-tetrahydro-pyrrolo[2,3-g]isoquinolin-5-one (0.229 g, 1 mmole, compound 1 above) and triethylamine (1 mmole) in CH$_2$Cl$_2$ (15 mL) was treated with benzoyl chloride (1 equivalent) at 0° C. and the mixture stirred at room temperature for 16 hours. Water (25 mL) was added, the organics separated and washed with water (15 mL), brine (15 mL) and dried (MgSO$_4$). Filtration and concentration in vacuo gave the required amide as a yellow colored oil (0.26 g, 78% yield). A THF solution (15 mL) of the amide was cooled to 0° C. under a N2 atmosphere and treated with the dropwise addition of lithium aluminum hydride (1M THF, 1 mL). The mixture was refluxed for 30 minutes, cooled to 0° C. and the excess hydride reagent treated with saturated NH$_4$Cl solution. The mixture was filtered, concentrated in vacuo, dissolved in ethyl acetate (15 mL), washed with water (2×20 mL), brine (15 mL) and dried over anhydrous sodium sulfate. Filtration and concentration in vacuo afforded the titled amine as a yellow oil.

MS(ESI) m/e 320 (M+H)+

Elemental Analysis for: C20H21N3O Calculated: C, 75.21; H, 6.63; N, 13.16. Found: C, 75.03; H, 6.59; N, 13.29.

Pharmaceutical Composition

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific disease must be subjectively determined by the attending physician. The novel method of the invention for treating conditions related to or are affected by the 5-HT7 receptor comprise administering to warm-blooded animals, including humans, an effective amount of at least one compound of Formula (1) and its non-toxic, pharmaceutically acceptable addition salts. The compounds may be administered orally, rectally, parenterally or topically to the skin and mucosa. The usual daily dose is depending on the specific compound, method of treatment and condition treated. The usual daily dose is 0.01–1000 mg/Kg for oral application, preferably 0.5–500 mg/Kg, and 0.1–100 mg/Kg for parenteral application, preferably 0.5–50 mg/Kg.

What we claim is:

1. A compound of Formula 1

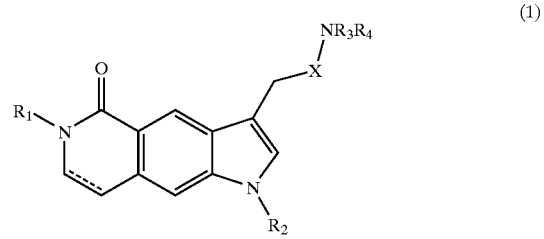

wherein:
R1 is hydrogen, alkyl of 1 to 8 carbon atoms, cycloalkyl of 3 to 8 carbon atoms, heterocycloalkyl of 3 to 8 members, alkylcycloalkyl of 4 to 9 carbon atoms, alkylheterocycloalkyl of 4 to 9 members or (CH2)mAr or (CH2)mHet;

R2 is hydrogen, alkyl of 1 to 8 carbon atoms, (CH2)nAr or (CH2)nHet;

R3 is hydrogen, alkyl of 1 to 8 carbon atoms, alkylcycloalkyl of 4 to 9 carbon atoms, alkylheterocycloalkyl of 4 to 9 members, (CH2)nAr or (CH2)nHet;

R4 is hydrogen or alkyl of 1 to 8 carbon atoms;

R is hydrogen or alkyl of 1 to 4 carbon atoms;

X is [(CH=CH)R]n, (CH$_2$)n, or [(C≡C)R]n, CHR(CH$_2$)n, CR$_2$(CH$_2$)n;

a dashed line represents an optional double bond;

m is an integer selected from 1 or 2; and n is an integer selected from 0, 1 or 2, or pharmaceutically acceptable salts thereof.

2. A compound of claim 1 wherein R1, R2, R3 and R4 are independently selected from hydrogen or alkyl.

3. A compound of claim 1 which is 3-(2-amino-ethyl)-1,6,7,8-tetrahydro-pyrrolo-[2,3-g]isoquinolin-5-one.

4. A compound of claim 1 which is 3-(2-amino-ethyl)-6-benzyl-1,6,7,8-tetrahydro-pyrrolo[2,3-g]isoquinolin-5-one.

5. A compound of claim 1 which is 3-(2-amino-ethyl)-6-benzylpyrrolo[2,3-g]isoquinolin-5-one.

6. A compound of claim 1 which is 3-(2-N-Benzylamino-ethyl)-1,6,7,8-tetrahydro-pyrrolo[2,3-g]isoquinolin-5-one.

7. A pharmaceutical composition comprising a compound of Formula I

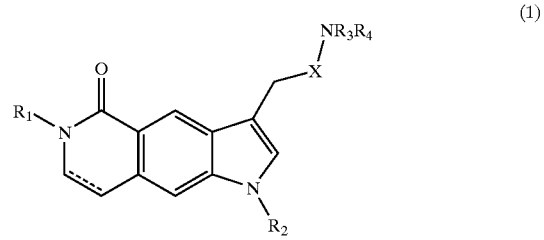

wherein:
R1 is hydrogen, alkyl of 1 to 8 carbon atoms, cycloalkyl of 3 to 8 carbon atoms, heterocycloalkyl of 3 to 8 members, alkylcycloalkyl of 4 to 9 carbon atoms, alkylheterocycloalkyl of 4 to 9 members or (CH2)mAr or (CH2)mHet;

R2 is hydrogen, alkyl of 1 to 8 carbon atoms, (CH2)nAr or (CH2)nHet;

R3 is hydrogen, alkyl of 1 to 8 carbon atoms, alkylcycloalkyl of 4 to 9 carbon atoms, alkylheterocycloalkyl of 4 to 9 members, (CH2)nAr or (CH2)nHet;

R4 is hydrogen or alkyl of 1 to 8 carbon atoms;
R is hydrogen or alkyl of 1 to 4 carbon atoms;
X is [(CH=CH)R]n, (CH$_2$)n, or [(C≡C)R]n, CHR(CH$_2$)n, CR$_2$(CH$_2$)n;
a dashed line represents an optional double bond;
m is an integer selected from 1 or 2; and
n is an integer selected from 0, 1 or 2, or pharmaceutically acceptable salts thereof, and a pharmaceutical carrier or excipient.

* * * * *